United States Patent
Pois et al.

(10) Patent No.: US 10,119,925 B2
(45) Date of Patent: *Nov. 6, 2018

(54) METHODS AND SYSTEMS FOR MEASURING PERIODIC STRUCTURES USING MULTI-ANGLE X-RAY REFLECTANCE SCATTEROMETRY (XRS)

(71) Applicant: NOVA MEASURING INSTRUMENTS INC., Santa Clara, CA (US)

(72) Inventors: Heath A. Pois, Fremont, CA (US); David A. Reed, Belmont, CA (US); Bruno W. Schueler, San Jose, CA (US); Rodney Smedt, Los Gatos, CA (US); Jeffrey T. Fanton, Los Altos, CA (US)

(73) Assignee: Nova Measuring Instruments Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/451,104

(22) Filed: Mar. 6, 2017

(65) Prior Publication Data

US 2017/0176354 A1 Jun. 22, 2017

Related U.S. Application Data

(63) Continuation of application No. 14/161,942, filed on Jan. 23, 2014, now Pat. No. 9,588,066.

(51) Int. Cl.
*G01N 23/201* (2018.01)
*H01L 21/66* (2006.01)

(52) U.S. Cl.
CPC ..... *G01N 23/201* (2013.01); *G01N 2223/054* (2013.01); *H01L 22/12* (2013.01)

(58) Field of Classification Search
CPC ...... G01N 23/201; G01N 23/20; G01N 23/04; G01N 23/20066; G01N 2223/054; G01N 2223/1016; G01N 21/9501; G01N 21/956; G01V 5/0025; A61B 6/483
See application file for complete search history.

(56) References Cited

U.S. PATENT DOCUMENTS

| | | |
|---|---|---|
| 5,619,548 A | 4/1997 | Koppel |
| 5,963,329 A | 10/1999 | Conrad et al. |
| 6,556,652 B1 | 4/2003 | Mazor et al. |

(Continued)

OTHER PUBLICATIONS

International Preliminary Report on Patentability from PCT/US2015/011753 dated Aug. 4, 2016, 10 pgs.

(Continued)

*Primary Examiner* — Hoon Song
(74) *Attorney, Agent, or Firm* — Womble Bond Dickinson (US) LLP

(57) ABSTRACT

Methods and systems for measuring periodic structures using multi-angle X-ray reflectance scatterometry (XRS) are disclosed. For example, a method of measuring a sample by X-ray reflectance scatterometry involves impinging an incident X-ray beam on a sample having a periodic structure to generate a scattered X-ray beam, the incident X-ray beam simultaneously providing a plurality of incident angles and a plurality of azimuthal angles. The method also involves collecting at least a portion of the scattered X-ray beam.

25 Claims, 7 Drawing Sheets

(56) References Cited

U.S. PATENT DOCUMENTS

| | | | |
|---|---|---|---|
| 6,633,831 B2 | 10/2003 | Nikoonahad et al. | |
| 6,771,735 B2 | 8/2004 | Janik et al. | |
| 6,815,570 B1 | 11/2004 | Janik et al. | |
| 6,816,570 B2 | 11/2004 | Janik et al. | |
| 7,039,158 B1 | 5/2006 | Janik et al. | |
| 7,110,491 B2 | 9/2006 | Mazor et al. | |
| 7,483,513 B2 | 1/2009 | Mazor et al. | |
| 7,600,916 B2 | 10/2009 | Yokhin et al. | |
| 7,920,676 B2 | 4/2011 | Yun et al. | |
| 8,040,511 B1 | 10/2011 | Krishnan et al. | |
| 2004/0156474 A1* | 8/2004 | Yokhin | G01N 23/20 378/70 |
| 2006/0062351 A1* | 3/2006 | Yokhin | G01N 23/20008 378/86 |
| 2006/0126079 A1 | 6/2006 | Bareket et al. | |
| 2007/0223011 A1 | 9/2007 | Jin et al. | |
| 2008/0273662 A1 | 11/2008 | Yun et al. | |
| 2009/0262900 A1* | 10/2009 | Mitsuda | G21K 1/06 378/145 |
| 2012/0086940 A1 | 4/2012 | Shih et al. | |

OTHER PUBLICATIONS

International Search Report and Written Opinion from PCT/US2015/011753 dated Apr. 29, 2015, 13 pgs.

Murnane, et al. "Scatterometry for 0.24 um-0.70 um developed photoresist metrology," SPIE (1995), pp. 427-436, vol. 2439.

Yu, Zhaoning, et al. In situ real time process characterization in nanoimprint lithography using time-resolved diffractive scatterometry, Applied Physics Letters, vol. 85, No. 18, Nov. 2004, p. 4166-4168.

Lüken, Eike et al., "Growth monitoring of W/Si X-ray multilayers by X-ray reflectivity and kinetic ellipsometry," Nov. 4, 1994, vol. 2253, pp. 327-332.

Agnihotri, Dileep K. et al., "Applications of Fast X-Ray Reflectometry—A Tool for In-Situ Thin Film Analysis," JCPDS-International Centre for Diffraction Data 2001, Advances in X-ray Analysis, vol. 44, pp. 302-307.

Naudon, A. et al., "New Apparatus for Grazing X-ray Reflectometry in the Angle-Resolved Dispersive Mode," J. Appl. Cryst. (1989), 22, 460-464.

Non-Final Office Action from U.S. Appl. No. 14/161,942 dated Jun. 8, 2016, 16 pgs.

* cited by examiner

METHODS AND SYSTEMS FOR MEASURING PERIODIC STRUCTURES USING MULTI-ANGLE X-RAY REFLECTANCE SCATTEROMETRY (XRS)

CROSS-REFERENCE TO RELATED APPLICATIONS

This application is a continuation of U.S. patent application Ser. No. 14/161,942, filed on Jan. 23, 2014, the entire contents of which are hereby incorporated by reference herein.

BACKGROUND

1) Field

Embodiments of the invention are in the field of X-ray reflectance scatterometry (XRS) and, in particular, methods and systems for measuring periodic structures using multi-angle XRS.

2) Description of Related Art

As integrated circuit (IC) features continue to be scaled to ever smaller dimensions, constraints on metrology used to measure such features become overwhelming. For example, critical dimension scanning electron microscopy (CD-SEM) metrology has several drawbacks that are becoming more significant with each new generation of IC technology. Drawbacks can include (1) the well known charging problem that limits the achievable resolution for IC metrology applications, (2) radiation damage induced dimensional shrinking of resists, (3) incompatibility with some low-k dielectrics, and (4) CD-SEM is essentially a surface technique making it difficult to measure three dimensional (3D) profiles.

Similarly, optical critical dimension (OCD) metrology faces a number of fundamental difficulties, including (1) the relatively long wavelength used is typically significantly larger than the device feature size and therefore does not provide a simple and direct measurement, and (2) OCD requires extensive modeling and interpolation, thus compromising the measurement sensitivity. Furthermore, over the last decades, use of shorter and shorter wavelengths has been necessitated by the reduction of circuit feature size. Currently the most advanced OCD system uses deep ultraviolet (DUV) wavelengths. Further incremental reduction in wavelength is not practical because of the extremely low transmission of shorter wavelength radiation in solids or even in low vacuum. Numerous problems can arise as a consequence, including low probing depth, lack of suitable optics, and stringent vacuum requirements. Such fundamental limitations have made it practically impossible to extend these existing technologies to meet the critical dimensional control requirements of next generation IC fabrication.

Grazing-incidence small-angle scattering (GISAS) is a scattering technique used to study nanostructured surfaces and thin films. The scattered probe is either photons (Grazing-incidence small-angle X-ray scattering, GISAXS) or neutrons (Grazing-incidence small-angle neutron scattering, GISANS). In either case, an incident beam strikes a sample under a small angle close to the critical angle of total external x-ray reflection. The intense reflected beam as well as the intense scattering in the incident plane are attenuated by a rod-shaped beam stop. The diffuse scattering from the sample is typically recorded with an area detector. However, since incident angles used in GISAS techniques is usually less than a few degrees, and even as small as a fraction of a degree. Accordingly, when used to measure 3D structures, information obtained through GISAS may be limited since the incident beam is directed mostly along only the top surfaces of such 3D structures.

Thus, advances are needed in metrology of 3D structures.

SUMMARY

Embodiments of the present invention pertain to methods and systems for measuring periodic structures using multi-angle X-ray reflectance scatterometry (XRS).

In an embodiment, a method of measuring a sample by X-ray reflectance scatterometry involves impinging an incident X-ray beam on a sample having a periodic structure to generate a scattered X-ray beam, the incident X-ray beam simultaneously providing a plurality of incident angles and a plurality of azimuthal angles. The method also involves collecting at least a portion of the scattered X-ray beam.

In another embodiment, a system for measuring a sample by X-ray reflectance scatterometry includes an X-ray source for generating an X-ray beam having an energy of approximately 1 keV or less. The system also includes a sample holder for positioning a sample having a periodic structure. The system also includes a monochromator positioned between the X-ray source and the sample holder. The monochromator is for focusing the X-ray beam to provide an incident X-ray beam to the sample holder. The incident X-ray beam simultaneously has a plurality of incident angles and a plurality of azimuthal angles. The system also includes a detector for collecting at least a portion of a scattered X-ray beam from the sample.

DETAILED DESCRIPTION

Figure 1:
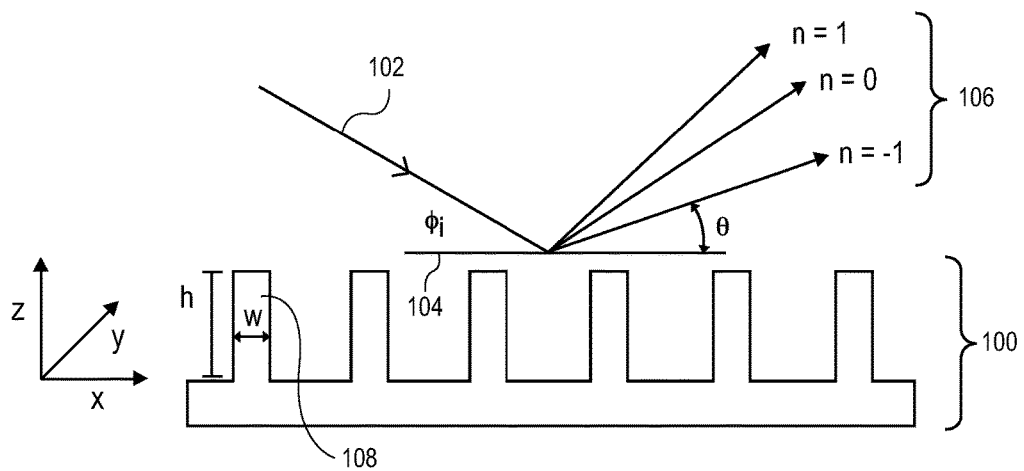
FIG. 1 illustrates a cross-sectional view of a periodic structure subjected to conventional scatterometry measurements using an incident beam having a single angle of incidence.

Methods and systems for measuring periodic structures using multi-angle X-ray reflectance scatterometry (XRS) are described. In the following description, numerous specific details are set forth, such as X-ray beam parameters and energies, in order to provide a thorough understanding of embodiments of the present invention. It will be apparent to one skilled in the art that embodiments of the present invention may be practiced without these specific details. In other instances, well-known features such as entire semiconductor device stacks are not described in detail in order to not unnecessarily obscure embodiments of the present invention. Furthermore, it is to be understood that the various embodiments shown in the Figures are illustrative representations and are not necessarily drawn to scale.

One or more embodiments described herein are directed to the use of an X-ray source configured in a manner that exploits simultaneous multiple incoming beam angles incident on a periodic (grating) structure for X-ray reflectance scatterometry measurements. Embodiments may enable detection of scattered light in two angular directions, as well as the use of reflected X-ray intensities to infer the shape and pitch of a periodic structure. Embodiments may provide suitable precision and stability measurements of the shape and size of complex two-dimensional (2D) and three-dimensional (3D) periodic structures in a production fab semiconductor environment. Such measurements may include shape profile of the periodic structures, and dimensions such as width, height and side-wall angle of the periodic structures.

To provide context, state-of-the-art shape metrology solutions utilize optical techniques with either single-wavelength or spectral sources nominally greater than 150 nanometers in wavelength. Spectral solutions are typically of fixed wavelength, and single wavelength sources that can vary in incident angle. Such solutions are in a wavelength/energy regime where $\lambda > d$, where $\lambda$ is the incident light source, and d is the fundamental dimension of the periodic structure. However, optical scatterometry is approaching its fundamental sensitivity limits.

In accordance with an embodiment of the present invention, by using wavelengths of light where $\lambda/d < 1$, higher order scattering orders are available for detection, and provide direct sensitivity to the parameter d. More specifically, by using wavelengths of light less than the width and height of the structures being measured, interference fringes of multiple cycles are available, and provide sensitivity to height, width and line shape. In an embodiment, by using multiple angles of incidence as well as azimuthal angles (e.g., relative to the direction of structure symmetry), three-dimensional information is obtained, providing three-dimensional shape sensitivity. The information obtained concerns dimensions that can critically affect device performance, and need to be controlled to very tight tolerances.

In order aid in conceptualizing concepts involved herein, FIG. 1 illustrates a cross-sectional view of a periodic structure subjected to conventional scatterometry measurements using an incident beam having a single angle of incidence. Referring to FIG. 1, a periodic structure 100 (also referred to as a grating structure) is subjected to a light beam 102. The light beam 102 has an angle of incidence, ϕi, relative to a horizontal plane 104 of the uppermost surface of the periodic structure 100. Scattered beams 106 are generated from the grating structure 100. The scattered beams 106 may include beams of differing scattered angle, each providing a different order of information of the grating structure 100. For example, as shown in FIG. 1, three orders, n=1, n=0, n=−1, are shown, where the scattered angle for the n=−1 order has an angle of θ relative to the horizontal plane 104 of the uppermost surface of the periodic structure 100. The arrangement of FIG. 1 is illustrative of conventional OCD or GISAS scatterometry approaches.

It is to be appreciated that use of the terms "periodic" or "grating" structure throughout refers to structures that are non-planar and, in some contexts, can all be viewed as three-dimensional structures. For example, referring again to FIG. 1, the periodic structure 100 has features 108 that protrude in the z-direction by a height, h. Each feature 108 also has a width, w, along the x-axis and a length along the y-axis (i.e., into the page). In some contexts, however, the term "three-dimensional" is reserved to describe a periodic or grating structure having a length along the y-axis that is on the same order as the width, w. In such contexts, the term "two-dimensional" is reserved to describe a periodic or grating structure having a length along the y-axis that is substantially longer than the width, w, e.g., several orders of magnitude longer. In any case, a periodic or grating structure is one having a non-planar topography within a region of measurement of, e.g., a semiconductor wafer or substrate.

Figure 2:
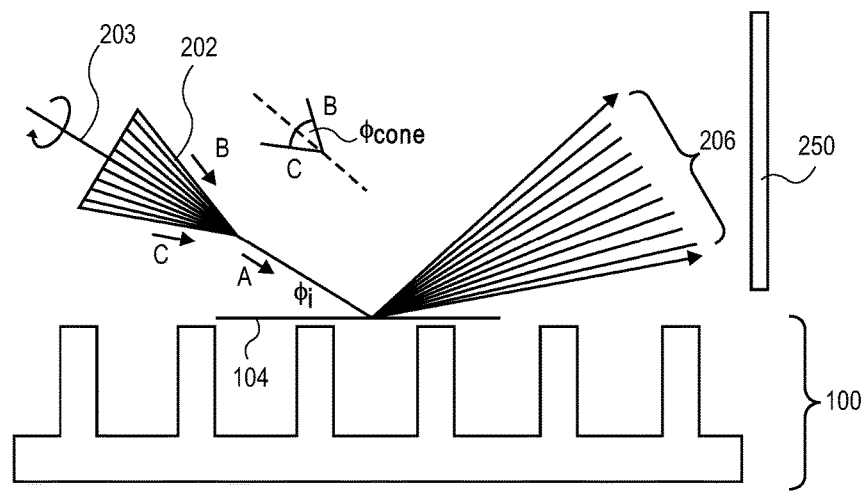
FIG. 2 illustrates a cross-sectional view of a periodic structure subjected to scatterometry measurements using an incident beam having multiple angles of incidence, in accordance with an embodiment of the present invention.

In contrast to FIG. 1, FIG. 2 illustrates a cross-sectional view of a periodic structure subjected to scatterometry measurements using an incident beam having multiple angles of incidence, in accordance with an embodiment of the present invention. Referring to FIG. 2, the periodic structure 100 is subjected to a conical X-ray beam 202. The conical X-ray beam 202 has a central axis 203 having an angle of incidence, ϕi, relative to the horizontal plane 104 of the uppermost surface of the periodic structure 100. As such, the conical X-ray beam 202 includes a portion, A, that has an incident angle ϕi. The conical beam 202 has a converging angle, ϕcone, which is taken between outermost portion, B, and outermost portion, C, of the conical beam 202. Since the conical beam 202 has the converging angle ϕcone, portions of the conical beam 202 near the outer portion of the cone have a different angle of incidence on the structure 100 than the portions of the conical beam 202 that are aligned with the central axis 202. Accordingly, the conical beam 202 simultaneously provides multiple angles of incidence for impinging on the structure 100, as taken relative to the horizontal plane 104. A scattered beam 206 is generated from the grating structure 100. The scattered beam 206 may include portions attributable to different orders of information of the grating structure 100, examples of which are described in greater detail below.

Figure 3:
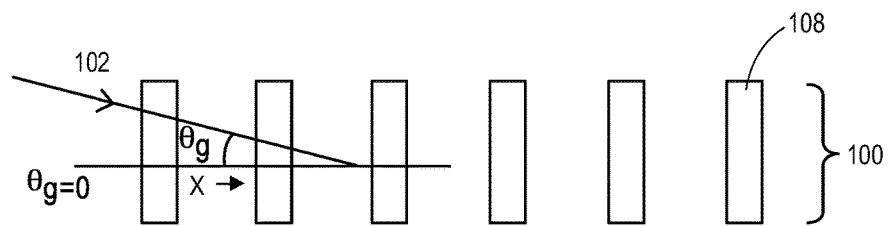
FIG. 3 illustrates a top-down view of a periodic structure subjected to conventional scatterometry measurements using an incident beam having a single azimuthal angle.

In addition to having an angle of incidence, an incident light beam can also have an azimuthal angle with respect to a periodic structure. Again for conceptual purposes, FIG. 3 illustrates a top-down view of a periodic structure subjected to conventional scatterometry measurements using an incident beam having a single azimuthal angle. Referring to FIG. 3, the periodic structure 100 is shown from above the protruding portions 108. Although not viewable in FIG. 1, the incident light beam 102 can further have an azimuthal angle, θg, relative to a direction, x, which is orthogonal to the protrusions 108 of the periodic structure 100. In some cases, θg is non-zero, as is depicted in FIG. 3. In cases where θg is zero, the direction of the beam 102 is along the x-direction, with respect to the top-down view. In all cases where conventional OCD or GISAS scatterometry approaches applied, however, the beam 102 has only one angle, θg. Thus, taking FIGS. 1 and 3 together, conventionally, scatterometry is performed using a light beam having a single angle of incidence, φi, and a single azimuthal angle, θg.

Figure 4A:
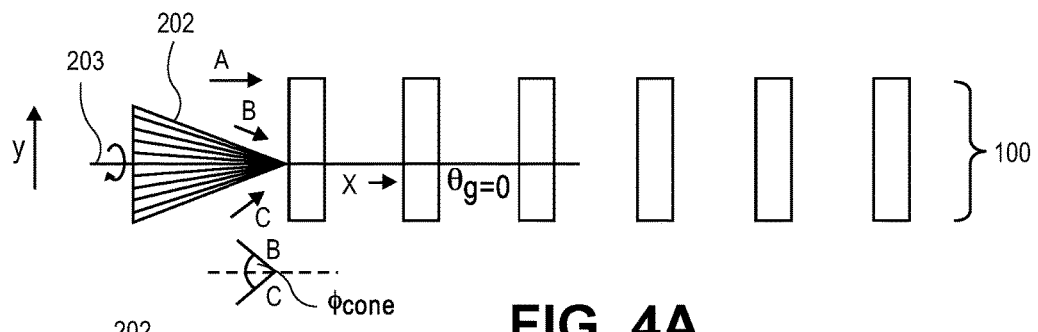
FIG. 4A illustrates a top-down view of a periodic structure subjected to scatterometry measurements using an incident beam having multiple azimuthal angles, with a central axis having a zero azimuthal angle, in accordance with an embodiment of the present invention.
Figure 4B:
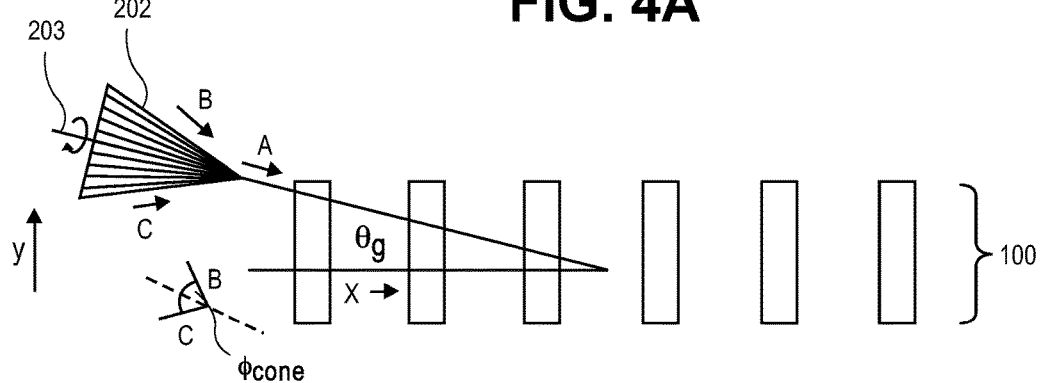
FIG. 4B illustrates a top-down view of a periodic structure subjected to scatterometry measurements using an incident beam having multiple azimuthal angles, with a central axis having a non-zero azimuthal angle, in accordance with an embodiment of the present invention.

In contrast to FIG. 3, FIGS. 4A and 4B illustrate top-down views of a periodic structure subjected to scatterometry measurements using an incident beam having multiple azimuthal angles, in accordance with an embodiment of the present invention. Referring to both FIGS. 4A and 4B, the periodic structure 100 is subjected to the conical X-ray beam 202 having the central axis 203, as described in association with FIG. 2. Although not viewable from FIG. 2, the conical X-ray beam 202 further has dimensionality along the y-direction. That is, the converging angle, φcone, taken between outermost portion, B, and outermost portion, C, of the conical beam 202, also provides a plurality of incident angles along the y-direction, e.g., to provide non-zero azimuthal angles of incidence.

Referring only to FIG. 4A, the central axis of the conical X-ray beam 202 has an angle θg of zero along the x-direction, with respect to the top-down view. As such, the portion A the conical X-ray beam 202 has a zero azimuthal angle. Nonetheless, the portions B and C of the conical X-ray beam 202 have non-zero azimuthal angles even though the central axis 203 of the conical X-ray beam 202 is orthogonal to the periodic structure 100.

Referring only to FIG. 4B, the central axis of the conical X-ray beam 202 has a non-zero angle, θg, along the x-direction, with respect to the top-down view. As such, the portion A the conical X-ray beam 202 has a non-zero azimuthal angle. Additionally, the portions B and C of the conical X-ray beam 202 have non-zero azimuthal angles different from the azimuthal angle of portion A of the beam 202.

In both cases illustrated in FIG. 4A and FIG. 4B, since the conical beam 202 has the converging angle φcone, portions of the conical beam 202 near the outer portion of the cone have a different azimuthal angle incident on the structure 100 than the portions of the conical beam 202 that are aligned with the central axis 202. Accordingly, the conical beam 202 simultaneously provides multiple azimuthal angles for impinging on the structure 100, as taken relative to the x-direction.

Thus, taking FIG. 2 and one of FIG. 4A or 4B together, in accordance with an embodiment of the present invention, a method of measuring a sample by X-ray reflectance scatterometry involves impinging an incident X-ray beam on a sample having a periodic structure. The X-ray beam has a conical shape to simultaneously provide multiple angles of incidence, φi, and multiple azimuthal angles, θg, as incident on the periodic structure. The impinging generates a scattered X-ray beam, a portion of which (if not all) can be collected in order to glean information about the periodic structure.

In an embodiment, the incident X-ray beam is a converging X-ray beam having a converging angle, φcone, approximately in the range of 20-40 degrees. In one such embodiment, a central axis of the converging X-ray beam has a fixed non-zero incident angle, φi, and an azimuthal angle, θg, of zero relative to the sample, as was described in association with FIG. 4A. In another such embodiment, a central axis of the converging X-ray beam has a fixed non-zero incident angle, φi, and a non-zero azimuthal angle, θg, relative to the sample, as was described in association with FIG. 4B. In either case, in a specific embodiment, the central axis of the converging X-ray beam has the fixed non-zero incident angle approximately in the range of 10-15 degrees from horizontal. In another specific embodiment, the outermost portion of the conical shape of the beam and closest portion to the periodic structure, e.g., portion C as shown in FIG. 2, has an angle of approximately 5 degrees relative to a horizontal plane of the periodic structure.

In other embodiments, an example of which is described in greater detail below, it may be preferable to use a narrower conical shape. For example, in an embodiment, the incident X-ray beam is a converging X-ray beam having a converging angle approximately in the range of 2-10 degrees. In one such embodiment, a central axis of the converging X-ray beam has a fixed non-zero incident angle, φi, and an azimuthal angle, θg, of zero relative to the sample, as was described in association with FIG. 4A. In another such embodiment, a central axis of the converging X-ray beam has a fixed non-zero incident angle, φi, and a non-zero azimuthal angle, θg, relative to the sample, as was described in association with FIG. 4B.

In an embodiment, a low energy X-ray beam is impinged on the periodic structure. For example, in one such embodiment, the low energy X-ray beam has an energy of approximately 1 keV or less. Use of such a low energy source can allow for larger incident angles yet with a smaller achievable spot size. In one embodiment, the low energy X-ray beam is a Kα beam generated from a source such as, but not limited to, carbon (C), molybdenum (Mo) or Rhodium (Rh).

In an embodiment, the low energy X-ray beam is focused using a toroidal multilayer monochromator prior to impinging on the periodic structure. In one such embodiment, the monochromator provides an incident angle range of approximately +/−30 degrees and an azimuth angle range of approximately +/−10 degrees. In a specific such embodiment, the toroidal multilayer monochromator provides an incident angle range of approximately +/−20 degrees. It is to be appreciated that the conical X-ray beams described herein may not, or need not, be collimated. For example, in one embodiment, between focusing the beam at the above described monochromator and impinging the focused beam on the periodic sample, the beam is not subjected to collimation. In one embodiment, the focused low energy X-ray beam is impinged on the sample at an incident angle range less than the angle of a nominal first-order angle at zero degrees.

Referring again to FIG. 2, in an embodiment, at least a portion of the scattered X-ray beam 206 is collected using a detector 250. In one such embodiment, a two-dimensional detector is used to simultaneously sample scattered signal intensity of the portion of the scattered X-ray beam 206 scattered from the plurality of incident angles and the plurality of azimuthal angles. The collected signal may then be subjected to scatterometry analysis, e.g., where inversion of scatter data is compared to theory to determine structural details of the periodic structure 100. In one such embodiment, a shape of the periodic structure of a sample is estimated by inversion of scattering solutions relative to the sampled scattered signal intensity, e.g., by rigorously solving Maxwell's equations on the periodic structure. In an embodiment, the X-ray beam impinged on the sample has a wavelength less than a periodicity of the periodic structure 100. Thus, the probing wavelength is comparable to or less than fundamental structural dimensions, providing a richer set of data from the scattered beam 206 as compared to OCD scatterometry.

As described above, in an embodiment, the incident conical X-ray beam used for XRS is a converging X-ray beam having a converging angle, φcone, approximately in the range of 20-40 degrees. Such a relatively broad cone angle may generate a scattered beam that includes higher order diffraction data in addition to zero-order reflection data. Thus, in one embodiment, both zero order and higher order information are obtained in parallel with a single impinging operation.

In other scenarios, it may be desirable to separate zero order reflection data from higher order diffraction data. In one such embodiment, a relatively narrower cone angle may be used, e.g., the incident X-ray beam is a converging X-ray beam having a converging angle approximately in the range of 2-10 degrees. More than one single measurement may be performed using the relatively narrower cone angle. For example, in one embodiment, a first measurement is made where the central axis of the converging beam has an azimuthal angle of zero, as described in association with FIG. 4A. A second measurement is then made where the central axis of the converging beam has a non-zero azimuthal angle, as described in association with FIG. 4B. In a specific embodiment, in a sequential manner, the first measurement is performed to collect $0^{th}$ order but not $1^{st}$ order diffraction data for a sample having a periodic structure. The second measurement is performed to collect $1^{st}$ order but not $0^{th}$ order diffraction data for a sample having a periodic structure. In this way, zero order data can be separated from higher order data at the time of generating the scattered beam.

Pertaining again to both the parallel and sequential approaches, in accordance with embodiments described herein, X-ray reflectance scatterometry is used to separate different orders on an array detector by approaching in a non-zero azimuth. In many cases it is the higher orders that are more useful. By cleanly obtaining all the orders in parallel, in one case, throughput can be enhanced. However, sequential approaches may also be used. Furthermore, a very focused beam is used to probe at a variety of incidence angles rather than at a single angle of incidence. In one embodiment, the beam is not collimated since for a collimated beam, a sample would require rotation with data taken serially. By capturing a higher order, use of a very small incidence angle is not needed in order to obtain a strong reflected beam. By contrast, in an embodiment, an angle of incidence of, e.g., 10 degrees to 15 degrees can be used even in the case where a specular (0-order) reflected beam is relatively weak but the −1 order, for example, is very strong.

In either case described above, whether collected in parallel or sequentially, embodiments described herein can be used to acquire data from both the zero order (specular) reflection and from the diffracted (higher) orders. Conventional solutions have emphasized using either zero order or diffracted (higher) orders, but not both. Embodiments described herein can further be distinguished from prior disclosed scatterometry approaches, a couple examples of which are described below.

In a first previously described approach, U.S. Pat. No. 7,920,676 to Yun et al. describes a CD-GISAXS system and method. The described approach involves analyzing the diffraction pattern of scattered X-rays generated from a collimated beam and analyzing multiple orders of the diffracted light. Lower energy is used to provide a higher-convergence beam because the diffraction orders are spaced farther apart. However, the orders are still fairly closely spaced and the convergence angles described are in microradians. Furthermore, diffraction is not collected for a multitude of incidence angles.

By contrast, in accordance with one or more embodiments described herein, a wide range of incidence angles is used in a single beam. In the present approach, diffracted orders (other than zero-order) do not actually have to be captured to be useful. However, the +/−1 orders can have different sensitivities to grating characteristics (in particular, the pitch), so, in one embodiment, at least one extra order is captured when possible. Even so, the bulk of the information is contained in the way the signal varies with incident angle. By contrast, in the U.S. Pat. No. 7,920,676, essentially one incident angle is used and information is gathered by looking at a multiplicity of diffracted orders.

Furthermore, in accordance with one or more embodiments described herein, the first order beam can be separated from the zero-order beam by moving the first-order beam to the side of the zero-order beam. In one such embodiment, the periodic or grating structure is approached at a non-zero azimuthal angle. In this way, a highly converging beam can be used while still achieving order separation. In an exemplary embodiment, by approaching the grating at a 45° azimuth angle (for the central axis of the converging beam), the +/−1 order diffracted beams are deflected to the side of the zero-order beam by a minimum of 10 degrees, and even more as the incidence angle is increased. In this case, a convergent beam of up to approximately 10 degrees can be used while avoiding overlap or data. It is to be appreciated that depending on the specifics of the grating pitch and the X-ray energy, the separation between orders can be made to be larger or smaller. Overall, in an embodiment, by collecting a multiplicity of incident and azimuthal angles simultaneously, more useful information is obtained than compared to a single shot of a collimated beam.

In a second previously described approach, U.S. Pat. No. 6,556,652 to Mazor et al. describes measurement of critical dimensions using X-rays. The described approach is not actually based on the diffraction of an X-ray beam at all. Instead, a "shadow" is created in a collimated beam. The shadow reflects off of a pattern (e.g., a linear grating structure). The contrast mechanism for the shadow is the difference in the critical angle for reflecting x-rays between a Si region at the bottom of a grating gap and the critical angle when passing first through ridge material (photoresist). By contrast, in accordance with embodiments described herein, a majority of information comes from signals at angles far above the critical angle.

As mentioned briefly above, and exemplified below, X-ray reflectance scatterometry (XRS) can be viewed as a type of X-ray reflectometry (XRR) as applied to two-dimensional and three-dimensional periodic or grating structures. Traditional XRR measurements involve the use of a single source X-ray that probes a sample over a range of angles. Varying optical path length differences with angle provides interference fringes that can be discerned to glean film property information such as film thickness and film density. However, in XRR, physics of the X-ray interaction with matter at higher source energies limits the angular range to a grazing incidence of typically less than approximately three degrees relative to sample horizontal plane. As a result, XRR has had limited production/inline viability. By contrast, in accordance with embodiments described herein, application of low-energy XRR/XRS enables the use of larger angles due to changing optical film properties with energy that lead to larger angles of signal sensitivity.

In an exemplary application of low energy XRS, fundamental semiconductor transistor building blocks may be measured and analyzed. For example, a critical dimension (CD) of a semiconductor device refers to a feature that has a direct impact on device performance or its manufacturing yield. Therefore, CDs must be manufactured or controlled to tight specifications. Examples of more conventional CDs include gate length, gate width, interconnect line width, line spacing, and line width roughness (LWR). Semiconductor devices are very sensitive to such dimensions, with small variations potentially leading to substantial impacts on performance, device failure, or manufacturing yield. As integrated circuit (IC) feature sizes of semiconductor devices continue to shrink, manufacturers face ever decreasing process windows and tighter tolerances. This has dramatically raised the accuracy and sensitivity requirements for CD metrology tools as well as the need for non-destructive measurement sampling early in the manufacturing cycle with minimal impact to productivity of the semiconductor device manufacturing plant or fab.

Non-planar semiconductor device fabrication has complicated matters even further. For example, semiconductor devices fabricated on raised channels having a non-planar topography often referred to as fins further include fin dimensions as additional CDs that must be accounted for. Such fin field effect transistor (fin-FET) or multi-gate devices have high-aspect ratio features, and the need for three-dimensional (3D) profile information on the fins of device structures, including sidewall angle, and top and bottom dimensions, has become critical. Consequently, the ability to measure the 3D profile provides far more valuable information than the conventional two-dimensional line width and spacing CD information.

Figure 5:
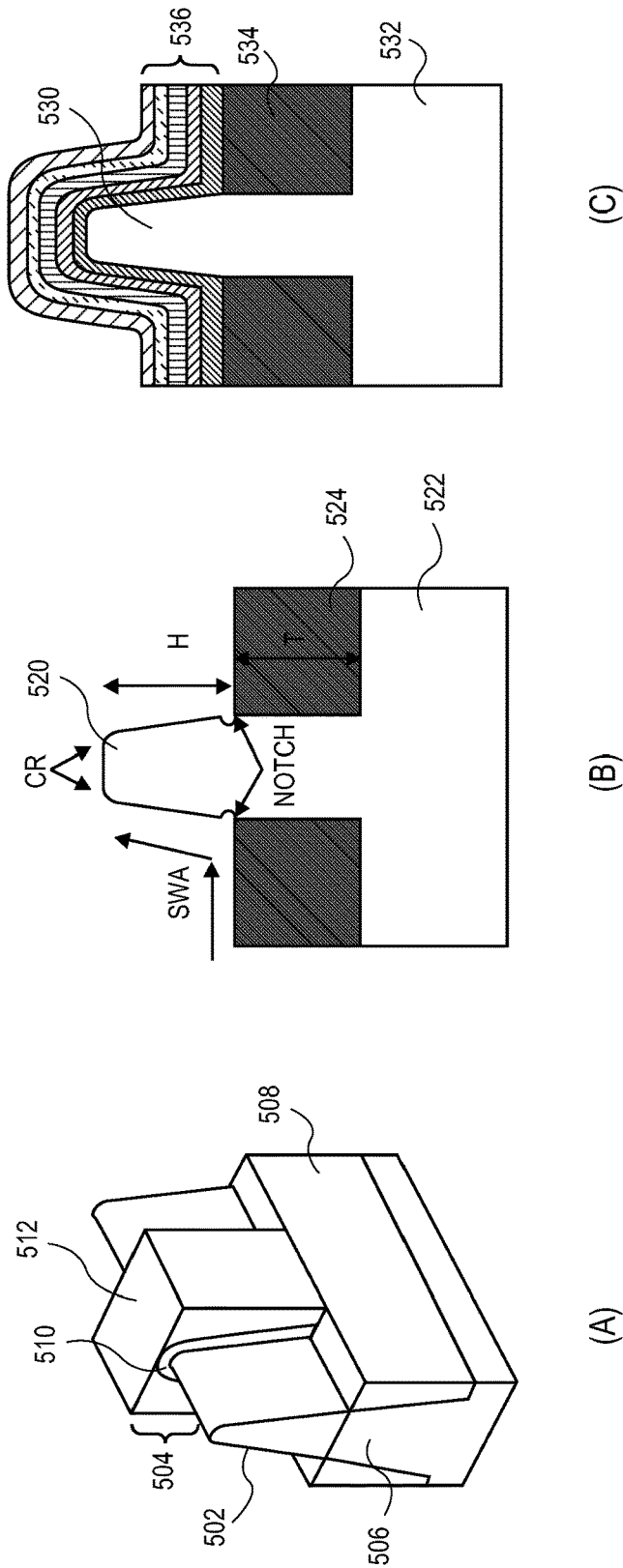
FIG. 5 illustrates aspects of exemplary fin-FET devices suitable for low energy X-ray reflectance scatterometry measurements, in accordance with an embodiment of the present invention.

FIG. 5 illustrates aspects of exemplary fin-FET devices suitable for low energy X-ray reflectance scatterometry measurements, in accordance with an embodiment of the present invention. Referring to FIG. 5, structure A illustrates an angled cross-sectional view of a semiconductor fin 502 having a gate electrode stack 504 disposed thereon. The semiconductor fin 502 protrudes from a substrate 506 which is isolated by shallow trench isolation (STI) regions 508. The gate electrode stack 504 includes a gate dielectric layer 510 and a gate electrode 512. Structure B illustrates a cross-sectional view of a semiconductor fin 520 protruding from a substrate 522 between STI regions 524. Aspects of structure B that may provide important information through XRS measurements include fin corner rounding (CR), fin sidewall angle (SWA), fin height (H), fin notching (notch), and STI thickness (T), all of which are depicted in structure B of FIG. 5. Structure C illustrates a cross-sectional view of a semiconductor fin 530 protruding from a substrate 532 between STI regions 534, and having a multilayer stack of films 536 thereon. The layers of the multilayer stack of films 536 may include material layers such as, but not limited to, titanium aluminum carbide (TiAlC), tantalum nitride (TaN) or titanium nitride (TiN). Comparing structures B and C, XRS measurements may be performed on a bare fin such as a bare silicon fin (structure B), or on a fin having different material layers disposed thereon.

Figure 6:
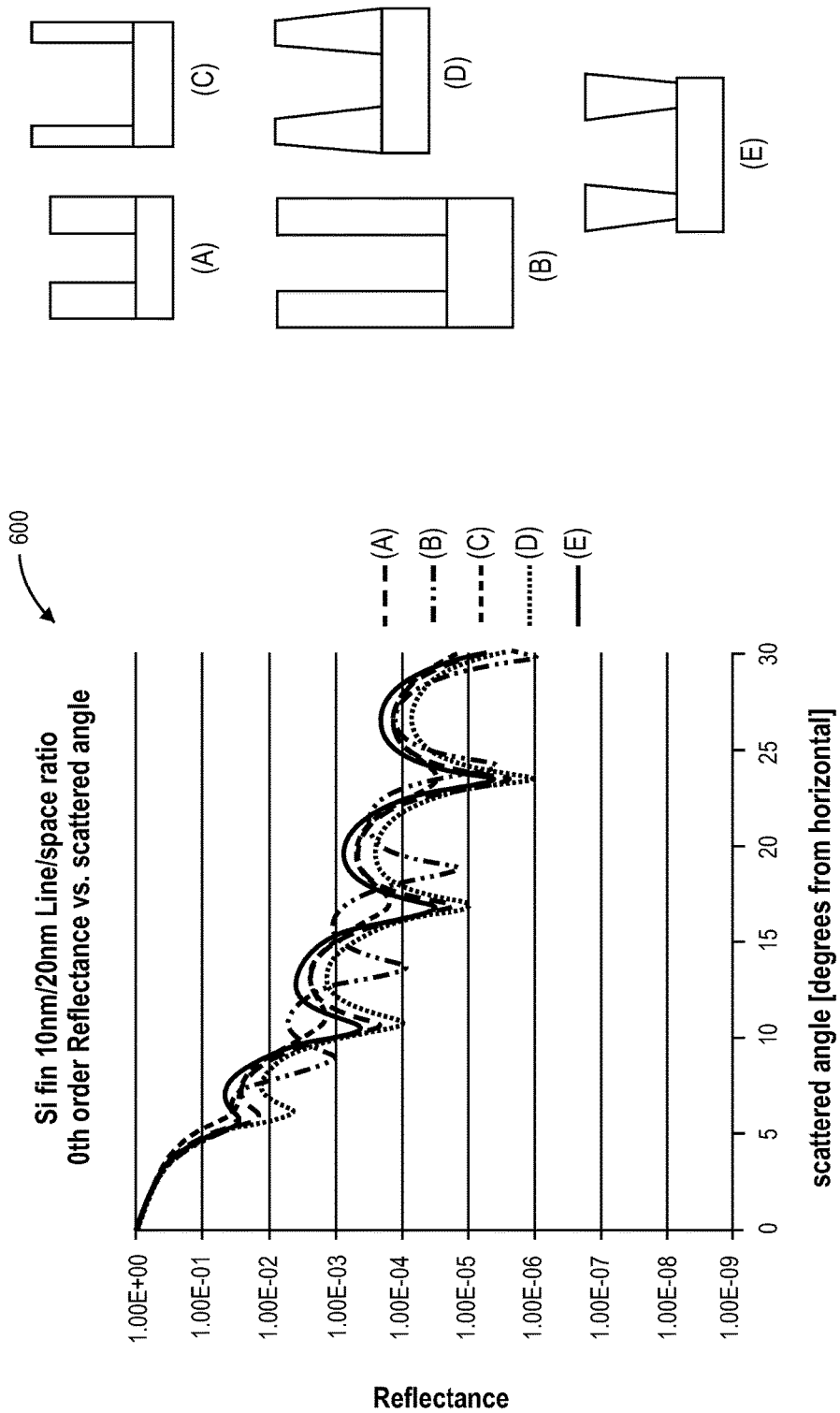
FIG. 6 includes a plot and corresponding structures of $0^{th}$ order reflectance versus scattered angle silicon (Si) fins having a periodic structure with 10 nm/20 nm line/space ratio, in accordance with an embodiment of the present invention.

FIG. 6 includes a plot 600 and corresponding structures (A)-(E) of $0^{th}$ order reflectance versus scattered angle silicon (Si) fins having a periodic structure with 10 nm/20 nm line/space ratio, in accordance with an embodiment of the present invention. Referring to FIG. 6, low energy XRS measurements can be used to distinguish between a nominal fin structure (structure A), a structure of increased fin height (structure B), a structure of decreased fin width (structure C), a structure of wider fin bottom CD versus fin top CD (structure D), and a structure of narrower fin bottom CD versus fin top CD (structure E). In this exemplar case, the Si fins are analyzed with $0^{th}$ order conical diffraction at 45 degrees to the periodic structure. It is to be appreciated that, in comparison to optical data, a reduced region of highest signal is achieved with fringes in data seen in plot 600 being a consequence of short wavelength.

Figure 7:
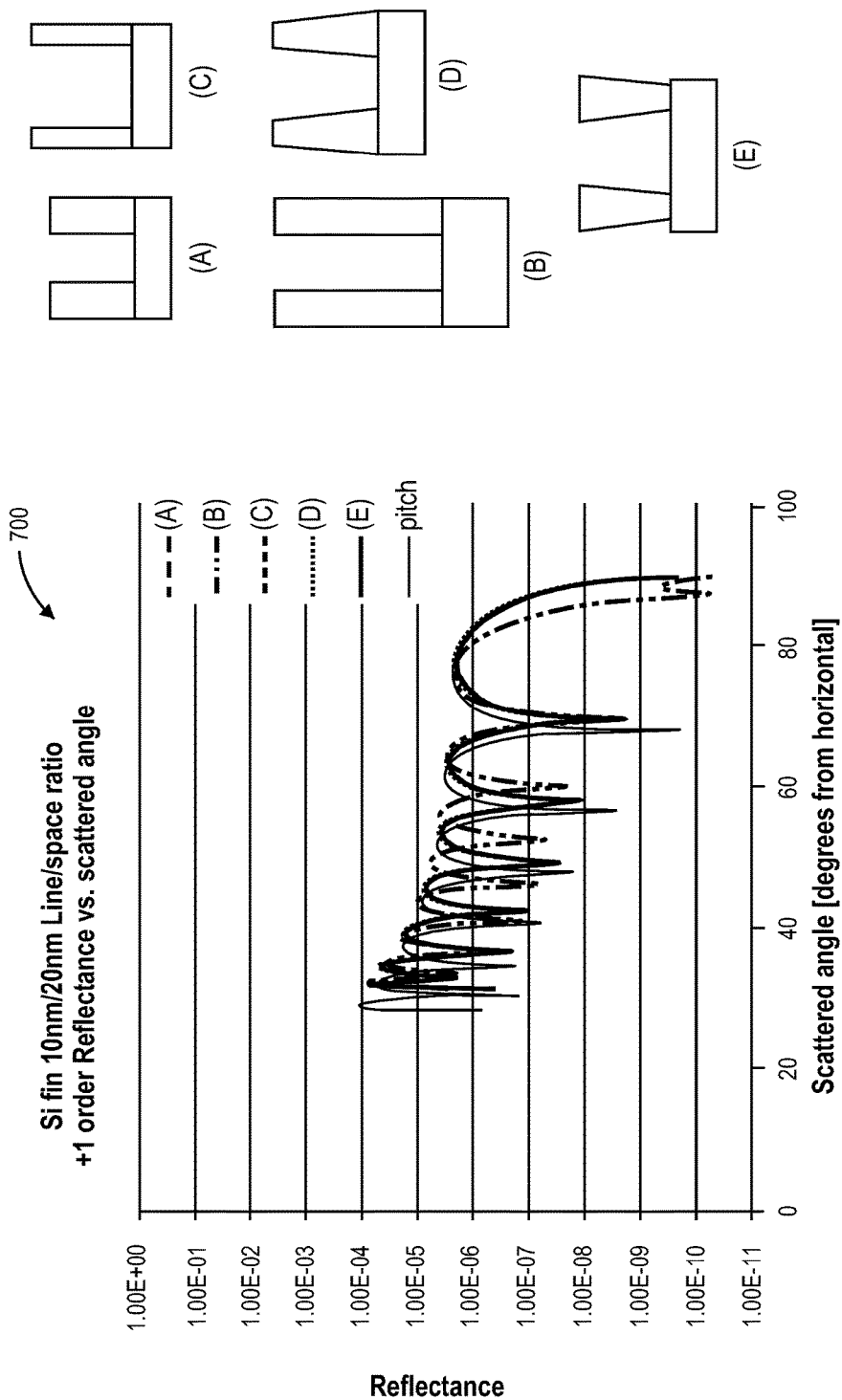
FIG. 7 includes a plot and corresponding structures of $1^{st}$ order reflectance versus scattered angle silicon (Si) fins having a periodic structure with 10 nm/20 nm line/space ratio, in accordance with an embodiment of the present invention.

FIG. 7 includes a plot 700 and corresponding structures (A)-(E) of $1^{st}$ order reflectance versus scattered angle silicon (Si) fins having a periodic structure with 10 nm/20 nm line/space ratio, in accordance with an embodiment of the present invention. Referring to FIG. 7, low energy XRS measurements can be used to distinguish between a nominal fin structure (structure A), a structure of increased fin height (structure B), a structure of decreased fin width (structure C), a structure of wider fin bottom CD versus fin top CD (structure D), and a structure of narrower fin bottom CD versus fin top CD (structure E). In this exemplar case, the Si fins are analyzed with $1^{st}$ order conical diffraction at 45 degrees to the periodic structure. Additionally, a structure of varying pitch has been included in plot 700. As shown in plot 700, $1^{st}$ order data is very sensitive to fin thickness (noting that structure B is separated significantly from the signals due to structures A and C-E). Also, $1^{st}$ order data is very sensitive to pitch variation in the periodic structure, noting that the spectrum for varied pitch is also significantly discernible from the other spectra.

In another aspect, an apparatus for performing X-ray reflectance scatterometry is described. In general, in an embodiment, such an apparatus includes a generic X-ray source along with a focusing monochromator that extends in two dimensions. The focusing monochromator allows for incident rays of light to strike a periodic sample at two varying incident angles, (i) incident to the plane of the periodic structure, and (ii) azimuthally, with respect to the symmetry of the structure (and at fixed incident angle). The detection of the scattered light is achieved by a two-dimensional (2D) detector, which simultaneously samples the scattered signal intensity across the range of scattered angles in the two angular directions. In one embodiment, the constraints of the monochromator that assure the detected signal is free of scattering order-overlap require that the incident angle range be less than the angle of the nominal first-order angle at 0 degree, i.e., $\theta=\sin^{-1}(1-\lambda/d)$. As a result of the use of light with a characteristic wavelength smaller than the period of the grating, higher order diffraction orders are accessible, and provide additional information regarding the grating structure. In addition, interference fringes of multiple thickness cycles are available to determine line height, width and shape. The final estimation of the shape and structure of the periodic structure is achieved via inversion of the scattering solutions compared to the 2D interference/scatter data.

Figure 8:
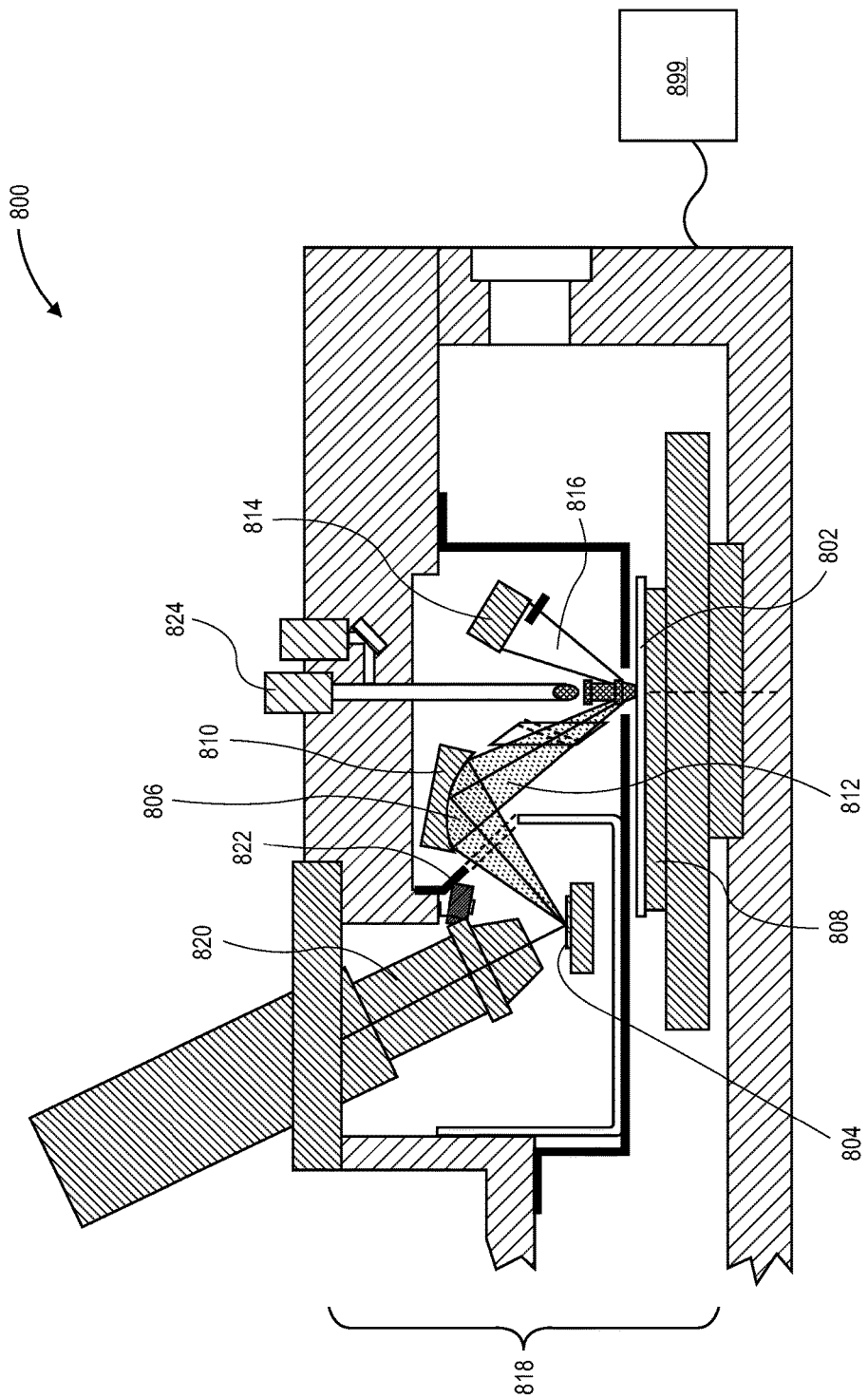
FIG. 8 is an illustration representing a periodic structure measurement system having X-ray reflectance scatterometry (XRS) capability, in accordance with an embodiment of the present invention.

As a more specific example, FIG. 8 is an illustration representing a periodic structure measurement system having XRS capability, in accordance with an embodiment of the present invention.

Referring to FIG. 8, a system 800 for measuring a sample 802 by X-ray reflectance scatterometry includes an X-ray source 804 for generating an X-ray beam 806 having an energy of approximately 1 keV or less. A sample holder 808 is provided for positioning the sample 802, the sample having a periodic structure. A monochromator 810 is positioned between the X-ray source 804 and the sample holder

802, in that the X-ray beam 806 travels from the X-ray source 804 to the monochromator 810 and then to the sample holder 808. The monochromator 810 is for focusing the X-ray beam 806 to provide an incident X-ray beam 812 to the sample holder 808. The incident X-ray beam 812 simultaneously has a plurality of incident angles and a plurality of azimuthal angles. The system 800 also includes a detector 814 for collecting at least a portion of a scattered X-ray beam 816 from the sample 802.

Referring again to FIG. 8, in an embodiment, the X-ray source 804, the sample holder 808, the monochromator 810 and the detector 814 are all housed in a chamber 818. In an embodiment, the system 800 further includes an electron gun 820. In one such embodiment, the X-ray source 804 is an anode and the electron gun is directed at the anode. In a particular embodiment, the anode is for generating low energy X-rays and includes a material such as, but not limited to, carbon (C), molybdenum (Mo) or Rhodium (Rh). In one embodiment, the electron gun 820 is an approximately 1 keV electron gun. Referring again to FIG. 8, a magnetic electron suppression device 822 is included between the X-ray source 804 and the monochromator 810.

In an embodiment, the monochromator 810 is a toroidal multilayer monochromator that provides an incident angle range of approximately +/−30 degrees and an azimuth angle range of approximately +/−10 degrees. In one such embodiment, the toroidal multilayer monochromator provides an incident angle range of approximately +/−20 degrees. In an embodiment, as described above, there is no intervening collimator between the monochromator 810 and the sample holder 808. The monochromator 810 may be positioned to provide a desired incident beam for XRS measurements. For example, in a first embodiment, the monochromator 810 is positioned relative to the sample holder 808 to provide a converging X-ray beam having a central axis with a fixed non-zero incident angle and an azimuthal angle of zero relative to a periodic structure of a sample 802. In a second embodiment, the monochromator 810 is positioned relative to the sample holder 808 to provide a converging X-ray beam having a central axis with a fixed non-zero incident angle and a non-zero azimuthal angle relative to a periodic structure of a sample 802. In an embodiment, the monochromator 810 is composed of alternating metal (M) layers and carbon (C) layers disposed on a glass substrate, where M is a metal such as, but not limited to, cobalt (Co) or chromium (Cr). In a particular such embodiment, a multilayer monochromator is provided for reflecting carbon (C) based K$\alpha$ radiation and includes approximately would be 100 repeating layers of Co/C or Cr/C with a period of about 4 nanometers, i.e., a period slightly less than the wavelength of the reflected beam which may be approximately 5 nanometers. In one such embodiment, the Co or Cr layers are thinner than the C layers.

The sample holder 808 may be a moveable sample holder. For example, in an embodiment, the sample holder 808 is rotatable to change an azimuth angle of a central axis of the X-ray beam 812 relative to a periodic structure of a sample 802. In an embodiment, the sample holder 808 is rotatable to provide orthogonal operation with eucentric rotation, enabling two or more sample rotations per measurement. In an embodiment, a navigation visual inspection apparatus 824 allows visual inspection of the sample holder 808, as is depicted in FIG. 8. In one such embodiment, a flip-in objective lens is included for a vision-based inspection system.

In an embodiment, the detector 814 is a two-dimensional detector. The two-dimensional detector may be configured for simultaneously sampling scattered signal intensity of the portion of the scattered X-ray beam 816 scattered from the plurality of incident angles and the plurality of azimuthal angles of the incident beam 812. In an embodiment, the system 800 further includes a processor or computing system 899 coupled to the two-dimensional detector. In one such embodiment, the processor 899 is for estimating a shape of the periodic structure of a sample 802 by inversion of scattering solutions relative to the sampled scattered signal intensity. In place of a two-dimensional detector, in another embodiment, a scanning slit may be implemented. In either case, the detector 814 can be configured to achieve approximately 1000 pixels of data collection across a dispersion range.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 9:
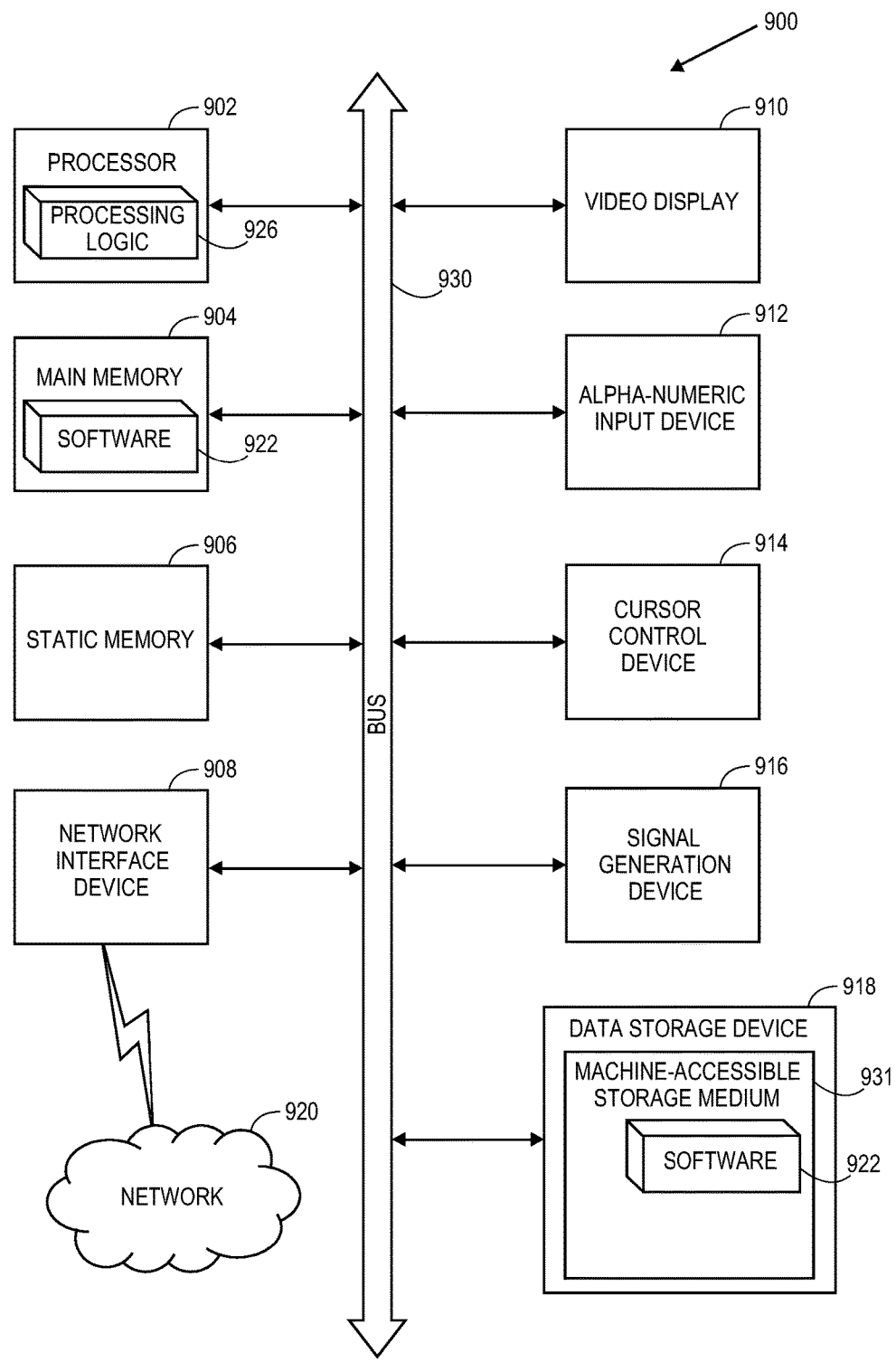
FIG. 9 illustrates a block diagram of an exemplary computer system, in accordance with an embodiment of the present invention.

FIG. 9 illustrates a diagrammatic representation of a machine in the exemplary form of a computer system 900 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. For example, in an embodiment, a machine is configured to execute one or more sets of instruction for measuring a sample by X-ray reflectance scatterometry. In one example, the computer system 900 may be suitable for use of computer system 899 of the above described XRS apparatus 800.

The exemplary computer system 900 includes a processor 902, a main memory 904 (e.g., read-only memory (ROM), flash memory, dynamic random access memory (DRAM) such as synchronous DRAM (SDRAM) or Rambus DRAM (RDRAM), etc.), a static memory 906 (e.g., flash memory, static random access memory (SRAM), etc.), and a secondary memory 918 (e.g., a data storage device), which communicate with each other via a bus 930.

Processor 902 represents one or more general-purpose processing devices such as a microprocessor, central processing unit, or the like. More particularly, the processor 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 902 may also be one or more special-purpose processing devices such as an application specific integrated circuit (ASIC), a field programmable gate array (FPGA), a digital signal processor (DSP), network processor, or the like. Processor 902 is configured to execute the processing logic 926 for performing the operations discussed herein.

The computer system 900 may further include a network interface device 908. The computer system 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 916 (e.g., a speaker).

The secondary memory 918 may include a machine-accessible storage medium (or more specifically a computer-readable storage medium) 931 on which is stored one or more sets of instructions (e.g., software 922) embodying any one or more of the methodologies or functions described herein. The software 922 may also reside, completely or at least partially, within the main memory 904 and/or within the processor 902 during execution thereof by the computer system 900, the main memory 904 and the processor 902 also constituting machine-readable storage media. The software 922 may further be transmitted or received over a network 920 via the network interface device 908.

While the machine-accessible storage medium 931 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In accordance with an embodiment of the present invention, a non-transitory machine-accessible storage medium has stored thereon instruction for performing a method of measuring a sample by X-ray reflectance scatterometry. The method involves impinging an incident X-ray beam on a sample having a periodic structure to generate a scattered X-ray beam. The incident X-ray beam simultaneously provides a plurality of incident angles and a plurality of azimuthal angles. The method also involves collecting at least a portion of the scattered X-ray beam.

Thus, methods and systems for measuring periodic structures using multi-angle X-ray reflectance scatterometry (XRS) have been described.

What is claimed is:

1. A method to characterize a sample using an X-ray reflectance scatterometry, the method comprising:
impinging an incident low energy X-ray beam having an energy of 1keV or less on a sample having a periodic structure to generate a first scattered X-ray beam, wherein the incident low energy X-ray beam is converging in an incidence and azimuth planes thereby providing simultaneously a plurality of incident angles and a plurality of azimuthal angles and having a range of incident angles that is greater than a range of azimuthal angles; and
collecting at least a portion of the first scattered X-ray beam.

2. The method of claim 1, wherein the range of incident angles is from +30 degrees to −30 degrees, and the range of azimuthal angles is from +10 degrees to −10 degrees.

3. The method of claim 1, wherein the converging incident X-ray beam has a converging angle in a range of from 20 degrees to 40 degrees.

4. The method of claim 1, wherein a central axis of the converging X-ray beam has a fixed azimuthal angle of zero relative to the sample.

5. The method of claim 1, wherein a central axis of the converging X-ray beam has a fixed non-zero incident angle in a range of 10 degrees to 15degrees from a horizontal plane.

6. The method of claim 2, wherein a central axis of the converging X-ray beam has a fixed non-zero azimuthal angle relative to the sample.

7. The method of claim 2, wherein a central axis of the converging X-ray beam has a fixed non-zero incident angle in a range of 10 degrees to 15degrees from a horizontal plane.

8. The method of claim 7, wherein the central axis of the converging X-ray beam has a fixed non-zero azimuthal angle relative to the sample.

9. The method of claim 8, further comprising:
positioning the central axis of the converging X-ray beam to the fixed non-zero azimuthal angle at the fixed non-zero incident angle relative to the sample; and, subsequently,
impinging the converging X-ray beam on the sample to generate a second scattered X-ray beam; and
collecting at least a portion of the second scattered X-ray beam.

10. The method of claim 9, wherein collecting the portion of the scattered X-ray beam comprises collecting $0^{th}$ order but not $1^{st}$ order diffraction data for the sample, and wherein collecting the portion of the second scattered X-ray beam comprises collecting $1^{st}$ order but not $0^{th}$ order diffraction data for the sample.

11. The method of claim 1, further comprising
generating the incident X-ray beam from a source selected from the group consisting of carbon (C), molybdenum (Mo) and Rhodium (Rh).

12. The method of claim 1, further comprising:
prior to the impinging, focusing the incident X-ray beam using a multilayer monochromator to generate the converging incident X-ray beam.

13. The method of claim 12, wherein the incident X-ray beam is not collimated between the focusing and the impinging.

14. The method of claim 1, the range of incident angles is less than the angle of a nominal first-order angle at zero degrees.

15. The method of claim 1, wherein the range of incident angles of from +20 degrees to −20 degrees is provided using a toroidal multilayer monochromator.

16. The method of claim 1, further comprising:
estimating a shape of the periodic structure of the sample by inversion of scattering solutions relative to the sampled scattered signal intensity.

17. The method of claim 1, wherein the converging incident X-ray beam has a wavelength that is less than a periodicity of the periodic structure.

18. A method to measure a sample using an X-ray reflectance scatterometry, the method comprising:
  impinging an incident low energy X-ray beam having an energy of 1keV or less on a sample having a periodic structure to generate a scattered X-ray beam, wherein the incident low energy X-ray beam is converging in an incidence and azimuth planes thereby providing simultaneously a plurality of incident angles and a plurality of azimuthal angles and having a range of incident angles that is greater than a range of azimuthal angles; and
  collecting at least a portion of the scattered X-ray beam using a two-dimensional detector to simultaneously sample a scattered signal intensity of the at least the portion of the scattered X-ray beam that is scattered from the range of incident angles and the range of azimuthal angles.

19. A system to measure a sample using an X-ray reflectance scatterometry, the system comprising:
  an X-ray source for generating an X-ray beam having an energy of 1 keV or less;
  a sample holder for positioning a sample having a periodic structure;
  a monochromator positioned between the X-ray source and the sample holder, the monochromator for focusing the X-ray beam to impinge an incident low energy X-ray beam on the sample to generate a scattered X-ray beam, wherein the incident low energy X-ray beam is converging in an incident angles and a plurality of azimuthal angles and having a range of incident angles that is greater than a range of azimuthal angles; and
  a 2-D detector for collecting at least a portion of the scattered X-ray beam from the sample.

20. The system of claim 19, wherein the X-ray source comprises an electron gun directed at an anode comprising a material selected from the group consisting of carbon (C), molybdenum (Mo) and Rhodium (Rh).

21. The system of claim 19, wherein the monochromator is a toroidal monochromator to provide the range of incident angles from +20 degrees to −20degrees.

22. The system of claim 19, wherein there is no intervening collimator between the monochromator and the sample holder.

23. The system of claim 19, wherein the sample holder is rotatable to change an azimuth angle of a central axis of the X-ray beam relative to the periodic structure of the sample.

24. The system of claim 19, wherein the sample holder is rotatable to provide an orthogonal operation with an eucentric rotation enabling two or more sample rotations per measurement.

25. The system of claim 19, further comprising:
  a processor coupled to the two-dimensional detector, the processor for estimating a shape of the periodic structure by inversion of scattering solutions relative to the sampled scattered signal intensity.

* * * * *